United States Patent
Li et al.

(10) Patent No.: US 10,589,263 B2
(45) Date of Patent: Mar. 17, 2020

(54) MARKOVNIKOV-SELECTIVE PALLADIUM CATALYST FOR CARBONYLATION OF ALKYNES WITH HETEROARENES

(71) Applicant: EVONIK DEGUSSA GMBH, Essen (DE)

(72) Inventors: Haoquan Li, Zhongshan (CN); Jie Liu, Solna (SE); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

(*) Notice: Subject to any disclaimer, the term of this patent is extended or adjusted under 35 U.S.C. 154(b) by 96 days.

(21) Appl. No.: 16/014,115

(22) Filed: Jun. 21, 2018

(65) Prior Publication Data
US 2019/0001316 A1 Jan. 3, 2019

(30) Foreign Application Priority Data
Jun. 29, 2017 (EP) .................... 17178595

(51) Int. Cl.
| | | |
|---|---|---|
| B01J 31/00 | (2006.01) | |
| B01J 31/24 | (2006.01) | |
| C07F 15/00 | (2006.01) | |
| C07F 9/572 | (2006.01) | |
| C07D 207/333 | (2006.01) | |
| B01J 31/18 | (2006.01) | |
| B01J 31/22 | (2006.01) | |

(52) U.S. Cl.
CPC ............ *B01J 31/24* (2013.01); *B01J 31/181* (2013.01); *B01J 31/2234* (2013.01); *B01J 31/2409* (2013.01); *C07D 207/333* (2013.01); *C07F 9/572* (2013.01); *C07F 15/006* (2013.01); *B01J 2231/321* (2013.01); *B01J 2531/824* (2013.01); *B01J 2540/40* (2013.01)

(58) Field of Classification Search
None
See application file for complete search history.

(56) References Cited

U.S. PATENT DOCUMENTS

| | | |
|---|---|---|
| 9,725,398 B2 | 8/2017 | Dong et al. |
| 2017/0022137 A1 | 1/2017 | Dong et al. |
| 2017/0022138 A1 | 1/2017 | Dong et al. |
| 2017/0022139 A1 | 1/2017 | Dong et al. |

OTHER PUBLICATIONS

Singapore Search Report for Application No. 10201805541Y dated Feb. 13, 2019 (2 pages).
Extend European Search Report dated Jan. 4, 2018, in European Patent Application No. 17178595.9 (12 pages).
Li, H., et al. The scope and mechanism of palladium-catalysed Markovnikov alkoxycarbonylation of alkenes. Nature Chemistry. Sep. 5, 2016. vol. 8, pp. 1159-1166.
Bhat, S., et al. Coordination of bis(azol-1-yl)methane-based bisphosphines towards $Ru^{II}$, $Rh^{I}$, $Pd^{II}$ and $Pt^{II}$: synthesis, structural and catalytic studies. Dalton Transactions. 2017. vol. 46, pp. 227-241.
Yang, Y., et al. Selective Ethylene Tri-/Tetramerization by in Situ-Formed Chromium Catalysts Stabilized by N,P-Based Ancillary Ligand Systems. ACS Catalysis. 2013. vol. 3, pp. 2353-2361.

*Primary Examiner* — Yun Qian
(74) *Attorney, Agent, or Firm* — Smith, Gambrell & Russell, LLP

(57) ABSTRACT

Markovnikov-selective palladium catalyst for carbonylation of alkynes is formed from a bisphosphite having formula (1):

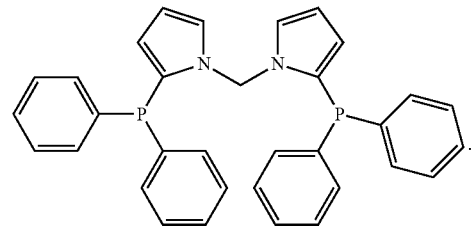

The carbonylation catalyst is suited for the preparation of a branched heteroarene-keto product from an alkyne substrate, CO and heterocycle in high yields with low amounts of the linear product.

2 Claims, No Drawings

MARKOVNIKOV-SELECTIVE PALLADIUM CATALYST FOR CARBONYLATION OF ALKYNES WITH HETEROARENES

The invention relates to Markovnikov-selective palladium catalyst for carbonylation of alkynes with heteroarenes.

The development of ligands plays a key role and provides significant innovations in homogenous catalysis and organic synthesis. Illustrative examples include polymerizations, organometallic coupling reactions, carbonylations, hydrogenations and metathesis. Although a plethora of nitrogen- and phosphorous-based ligands have been developed over the last decades, their rational design to afford highly active catalyst systems, which can easily be prepared and modified, continues to be an important topic in this area.

Among the privileged ligand classes known, especially bi- and multidentate derivatives create highly stable and selective organometallic complexes.

The problem addressed by the invention was that of providing a compound which is to have good properties as ligands in palladium catalyst for carbonylation of alkynes and reaches a good result regarding the yield of the carbonylation reaction.

The problem is solved by a compound according to claim 1,

Compound having the structure (1):

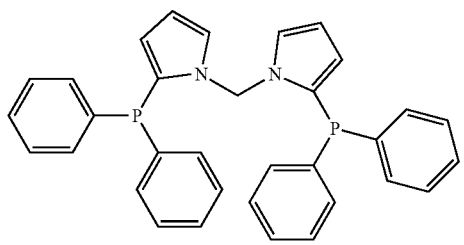

(1)

Additionally claimed is the use of the compound as ligand in a ligand-metal complex for catalysis of a carbonylation reaction.

Use of a compound described above in a ligand-metal complex for catalysis of a carbonylation reaction.

The process in which the compound is used as ligand in a ligand-metal complex for conversion of an olefin to an aldehyde is likewise claimed.

A process comprising the following process steps:
a) initially charging an alkyne,
b) adding an above-described compound and a substance including Pd,
c) feeding in N-methylpyrrole and CO,
d) heating the reaction mixture, with conversion of the alkyne to the product.

In this process, process steps a) to d) can be effected in any desired sequence.

In a preferred variant of the process, the metal atom is Rh,

The invention is illustrated in detail hereinafter by working examples.

Ligand Synthesis

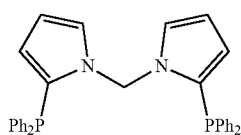

(1)

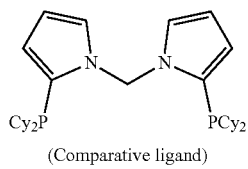

(Comparative ligand)

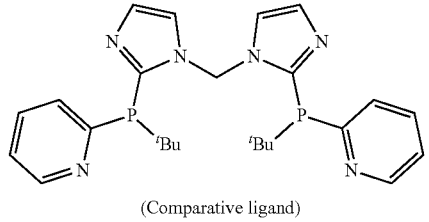

(Comparative ligand)

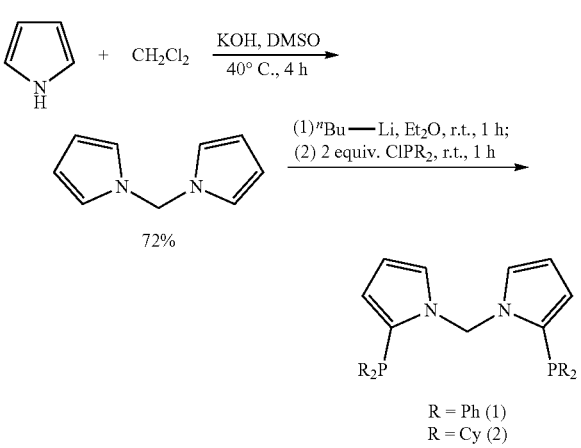

R = Ph (1)
R = Cy (2)

Synthesis of N,N'-dipyrrolylmethane

Pyrrole (9.00 ml, 130 mmol) was added to a stirred suspension of powdered potassium hydroxide (24 g, 0.43 mol, 3.31 equiv.) in DMSO (100 ml) at room temperature. After 1 h, the mixture was heated to 40° C. and DCM (6.32 ml, 98.6 mmol, 0.76 equiv.) was added slowly. The solution was heated at 40° C. for a further 4 h. Once cool, ether (100 ml) and water (100 ml) were added and the layers separated. The aqueous layer was extracted with ether three times, the combined organic extracts were washed with water three times, then brine, and dried with $MgSO_4$ and the solvent removed under reduced pressure to afford a pale yellow solid. Recrystallisation from chloroform gave 1,2-di(pyrrol-1-yl)methane in 72% yield.

Synthesis of N, N'-diimidazolmethane

Analogues to N,N'-dipyrrolylmethane

Synthesis of (1) and (2):

In a three nacked 100 ml round bottom flask, N, N'-dipyrrolylmethane (5 mmol) was dissolved in 15 ml of freshly distilled $Et_2O$ under argon. TMEDA (15 mmol) was added followed by n-BuLi (10.5 mmol, 1.6 M in hexane) at room temperature. The reaction mixture was stirring for 1 h at room temperature, a yellow suspension was obtained. Then the yellow suspension was slowly added via syringe to a solution of $ClPR_2$ (10 mmol in 15 ml $Et_2O$, R=Ph or Cy).

The mixture was further stirring for 1 h, then degassed water (10 ml) was added and the mixture was stirred to get a clear solution. The aqueous layer was extracted with Et$_2$O (2×15 ml) and the combined organic layers were washed with degassed water (10 ml). The solution was dried over Na$_2$SO$_4$ and concentrated to get a yellow viscous liquid which was recrystallized from ethanol. For yield and characterizations please see below.

Characterizations:

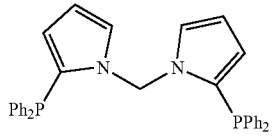

(1)

1.0 g, 39% yield (5 mmol scale, 97% purity), white solid.

$^1$H NMR (300 MHz, CD$_2$Cl$_2$) δ 7.23-7.18 (m, 20H), 6.85-6.83 (m, 2H), 6.17 (t, J=2.8 Hz, 2H), 6.00 (dd, J=3.6, 2.8 Hz, 2H), 5.83 (dd, J=3.6, 1.6 Hz, 2H);

$^{13}$C NMR (75 MHz, CD$_2$Cl$_2$) δ 137.1, 133.7, 129.1, 128.9, 127.8, 125.7, 119.8, 110.5, 58.1

$^{31}$P NMR (122 MHz, CD$_2$Cl$_2$) δ−33.0.

HRMS (ESI) [C$_{33}$H$_{52}$N$_2$P$_2$+H]$^+$ calculated mass 539.36785, measured mass 539.36811.

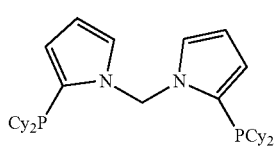

(2)

0.54 g, 20% yield (5 mmol scale, 95% purity), off white solid.

$^1$H NMR (300 MHz, d$^8$-Toluene) δ 7.18-7.15 (m, 2H), 6.53-6.51 (m, 2H), 6.40-6.38 (m, 2H), 6.31-6.29 (m, 2H), 1.86-1.56 (m, 24H), 1.25-1.06 (m, 20H);

$^{13}$C NMR (75 MHz, d$^8$-Toluene) δ 126.1, 124.3, 1161, 109.6, 57.0, 34.2, 30.4, 29.1, 27.1;

$^{31}$P NMR (122 MHz, d$^8$-Toluene) δ−31.0.

HRMS (ESI) [C$_{33}$H$_{52}$N$_2$P$_2$+H]$^+$ calculated mass 539.36785, measured mass 539.36811.

Synthesis of (3):

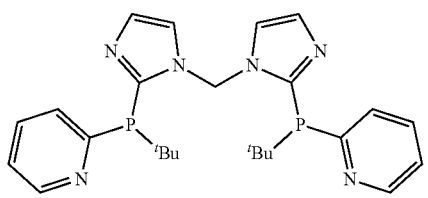

(3)

analogues to (1) and (2)

Catalyst Experiments

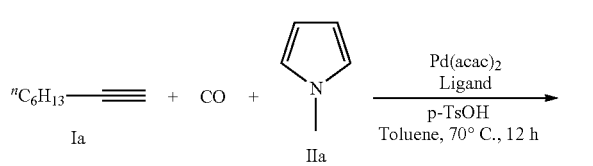

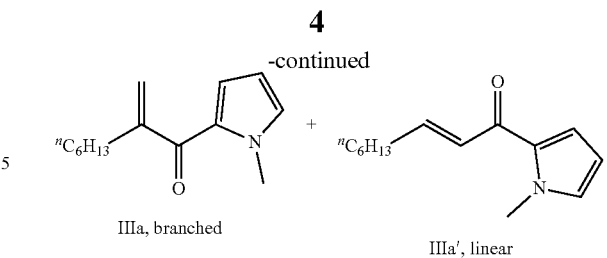

Catalyst Results

The results of the catalyst experiments are summarized in Tables 1;

TABLE 1

| Ligand | p (bar) | T (° C.) | t (h) | Pd(acac)$_2$ (mol) | Yield (%) |
|---|---|---|---|---|---|
| 1* | 40 | 70 | 12 | 2 | 88 |
| 2 | 40 | 70 | 12 | 2 | 0 |
| 3 | 40 | 70 | 12 | 2 | 0 |

*inventive compound
alkyne = 1-octyne

Reaction conditions: (Ia) (1.0 mmol), (IIa) (0.5 mmol), Pd(acac)$_2$ (2.0 mol %), Ligand (4.0 mol %), p-TsOH (10.0 mol %), CO (40 bar), Toluene (1.0 mL), 70° C., 12 h.

Further results of carbonylation experiments with different alkynes (I) are summarized in Table 2:

TABLE 2

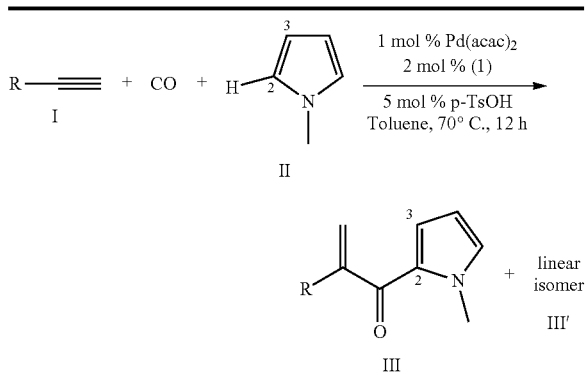

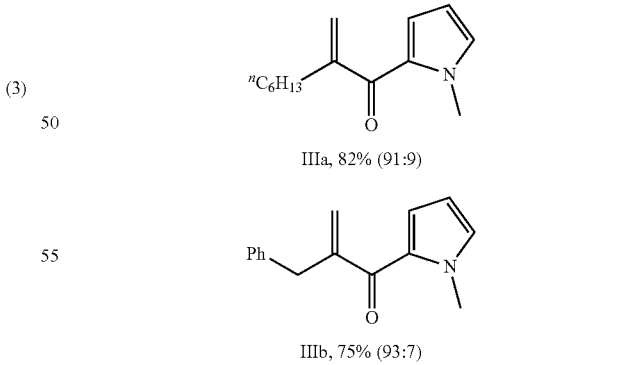

IIIa, 82% (91:9)

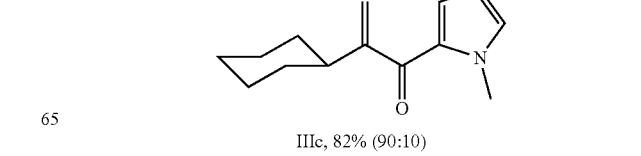

IIIb, 75% (93:7)

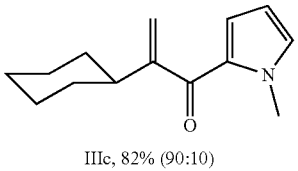 [SMILES: C=C(C(=O)c1cccn1C)C1CCCCC1]

IIIc, 82% (90:10)

TABLE 2-continued

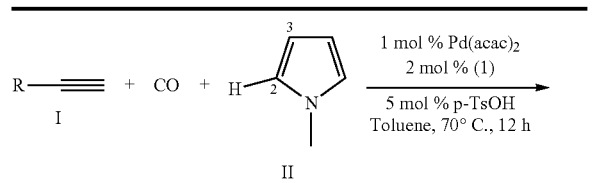

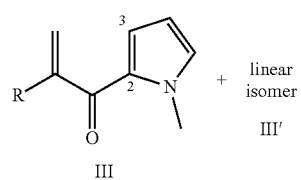

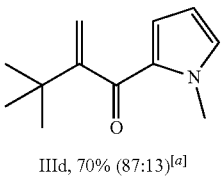

IIId, 70% (87:13)[a]

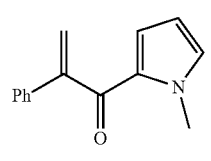

IIIe, 88% (99:1)

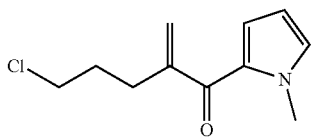

IIIf, 86% (88:12)

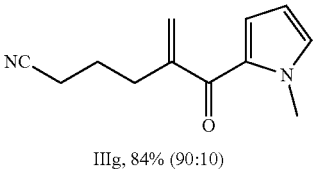

IIIg, 84% (90:10)

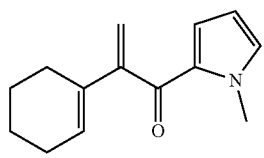

IIIh, 81% (99:1)

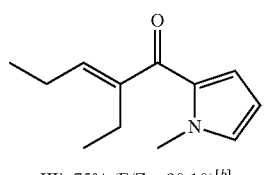

IIIi, 75% (E/Z = 90:10)[b]

TABLE 2-continued

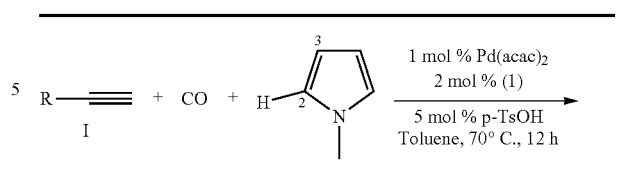

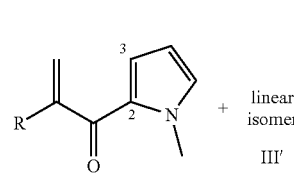

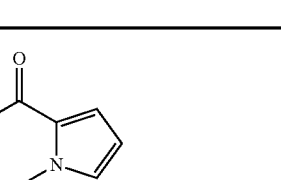

IIIj, 68% (E/Z = 93:7)[c]

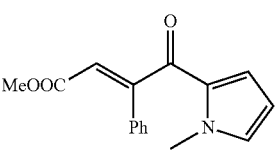

IIIk, 56% (E/Z = 99:1)[b]

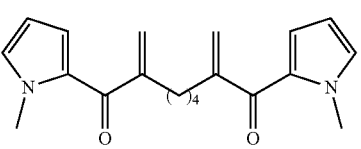

IIIl, 36% (b:l = 95:5)

Reaction condition: alkyne (I) (1.0 mmol), N-methylpyrrole (II) (0.5 mmol), Pd(acac)$_2$ (1.0 mol %), (1) (2.0 mol %), p-TsOH (5.0 mol %), CO (40 bar), Toluene (1.0 mL), 70° C., 12 h.

In each case, the yield of isolated compound (III) is given, and the number in the parenthesis indicates the (III/III') ratio determined by GC analysis.

[a] Reaction at 90° C.

[b] Reaction at 100° C. for 20 h.

[c] Reaction at 90° C. for 20 h.

It was shown on the basis of the experiments described above that the stated problem has been solved by the inventive compounds.

The invention claimed is:
1. Compound having the structure (1):

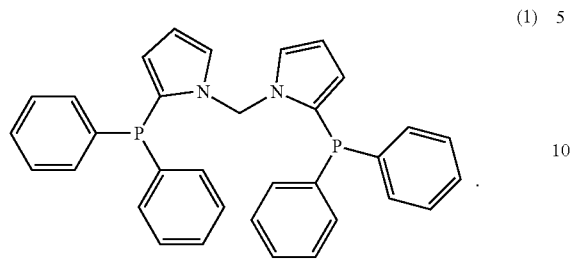

(1)

2. A process for Markovnikov-selective carbonylation of an alkyne in whose molecule there is one hydrogen atom bonded to a triply bonded carbon atom to form a heteroarene-keto product comprising the following process steps to form a reaction mixture:
   a) initially charging the alkyne,
   b) adding a compound according to claim 1 and a substance including Pd,
   c) feeding N-methylpyrrole and CO,
   d) heating the reaction mixture to react the alkyne with CO and N-methylpyrrole to form the heteroarene-keto product.

* * * * *